US006238873B1

United States Patent
Ames et al.

(10) Patent No.: US 6,238,873 B1
(45) Date of Patent: May 29, 2001

(54) METHODS OF SCREENING FOR AGONISTS AND ANTAGONISTS OF THE INTERACTION BETWEEN THE HUMAN KIAA0001 RECEPTOR AND LIGANDS THEREOF

(75) Inventors: Robert S. Ames, Havertown; Anne Romanic Arnold, Wynnewood, both of PA (US); Jonathan K. Chambers, Haslingfield (GB); James Joseph Foley, Radnor; Henry M. Sarau, Harleysville, both of PA (US); Brian R. Stewart, Welwyn (GB)

(73) Assignee: Smithkline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/303,524

(22) Filed: Apr. 30, 1999

Related U.S. Application Data

(60) Provisional application No. 60/083,957, filed on May 1, 1998.

(51) Int. Cl.[7] .................. G01N 33/53; G01N 33/566; G01N 33/66
(52) U.S. Cl. ..................... 435/7.2; 435/7.21; 436/501
(58) Field of Search ........................ 435/7.2, 7.21; 436/501

(56) References Cited

PUBLICATIONS

Nomura et al. *DNA Research*, vol. 1, pp. 27–35, 1994.*
Du, et al., "Modeling the G–Protein–Coupled Neuropeptide Y Y1 Receptor Agonist and Antagonist Binding Sites," *Protein Engineering*, 10(2): 109–117 (1997).
Turcatti, et al., "Probing the Binding Domain of the NK2 Receptor with Fluorescent Ligangs: Evidence That Heptapeptide Agonists and Antagonists Bind Differently," *Biochemistry*, 34(12): 3972–3980 (1995).
Negishi, et al., "Selective Coupling of Prostaglandin E Receptor EP3D to Gi and Gs Through Interaction of Alpha–Carboxylic Acid of Agonist and Arginine Residue of Seventh Transmembrane Domain," *J. Biol. Chem.*, 270(27): 16122–16127 (1995).
Gardella, et al., "Transmembrane Residues of the Parathyroid Hormone (PTH)/PTH–Related Peptide Receptor That Specifically Affect Binding and Signaling by Agonist Ligands," *J. Biol. Chem.*, 271(22): 12820–12825 (1996).
Sung, et al., "Angiotensin Type 1 Receptors Mediate Smooth Muscle Proliferation and Endothelin Biosynthesis in Rat Vascular Smooth Muscle," *J. Pharm. Exp. Ther.*, 271(1):429–437 (1994).
Pastoris, et al. "UDP–Glucose Effect on Phrenic Diaphragm Preparation of the Rat," *Farmaco [Sci].*, 36(8):721–728 (1981).
Pastoris, et al., "In Vitro Action of Uridine Diphosphate Glucose (UDPG) on Phrenic Diaphragm Preparations," *Farmaco [Sci.].*, 34(3):211–216 (1979).
Charlton, et al., "The Isolation and Characterization of a Novel G Protein–Coupled Receptor Regulated by Immunologic Challenge," *Brain Res.*, 764:141–148 (1997).
Berthillier, et al., "Molecular Weight of a Membrane Receptor of UDP–Glucose" *FEBS Lett.*, 56(2):256–258 (1975).
Frot–Coutaz, et al., A Receptor for UDP–Glucose in the Microsomal Membranes of Rat Hepatocytes, *FEBS Lett.*, 52(1):81–84 (1975).

* cited by examiner

*Primary Examiner*—Gary L. Kunz
*Assistant Examiner*—Stephen Gucker
(74) *Attorney, Agent, or Firm*—Elizabeth J. Hecht; Edward R. Gimmi; Charles M. Kinzig

(57) ABSTRACT

Disclosed are methods for discovering agonists and antagonists of the interaction between UDP-glucose, UDP-galactose, UDP-glucuronic acid, UDP-N-acetyl glucosamine, as well as related UDP sugars, and their cellular receptor, human KIAA0001, which may have utility in the treatment of several human diseases and disorders, including, but not limited to: infections such as bacterial, fungal, protozoan and viral infections, particularly infections caused by HIV-1 or HIV-2; pain; cancers; diabetes, obesity; anorexia; bulimia; asthma; Parkinson's disease; acute heart failure; hypotension; hypertension; urinary retention; osteoporosis; angina pectoris; myocardial infarction; restenosis; atherosclerosis; diseases characterized by excessive smooth muscle cell proliferation; aneurysms; wound healing; diseases characterized by loss of smooth muscle cells or reduced smooth muscle cell proliferation; stroke; ischemia; ulcers; asthma; allergies; benign prostatic hypertrophy; migraine; vomiting; psychotic and neurological disorders, including anxiety, schizophrenia, manic depression, depression, delirium, dementia, and severe mental retardation; degenerative diseases, such as neurodegenerative diseases and dyskinesias, such as Huntington's disease or Gilles dela Tourett's syndrome, among others.

6 Claims, 5 Drawing Sheets

Figure 1

ATCATGATTAATTCTACT**TCCACACAGCCTCCAGATGAATCCTGCTCTCAGAACCTCCTGAT
CACTCAGCAGATCATTCCTGTGCTGTACTGTATGGTCTTCATTGCAGGAATCCTACTCAATG
GAGTGTCAGGATGGATATTCTTTTACGTGCCCAGCTCTAAGAGTTTCATCATCTATCTCAAG
AACATTGTTATTGCTGACTTTGTGATGAGCCTGACTTTTCCTTTCAAGATCCTTGGTGACTC
AGGCCTTGGTCCCTGGCAGCTGAACGTGTTTGTGTGCAGGGTCTCTGCCGTGCTCTTCTACG
TCAACATGTACGTCAGCATTGTGTTCTTTGGGCTCATCAGCTTTGACAGATATTATAAAATT
GTAAAGCCT*C*TTTGGACTTCTTTCATCCAGTCAGTGAGTTACAGCAAACTTCTGTCAGTGAT
AGTATGGATGCTCATGCTCCTCCTTGCTGTTCCAAATATTATTCTCACCAACCAGA*g*TGTTA
GGGA*g*GTT*a*CACAAATAAAATGTATAGAACTGAAAAGTGAACTGGGACGGAAGTGGCACAAA
GCATCAAACTACATCTTCGTGGCCATCTTCTGGATAGTGTTTCTTTTGTTAATCGTTTTCTA
TACTGCTATCACAAAGAAAATCTTTAAGTCCCACCTTAAGTCAAGTCGGAATTCCACTTCGG
TCAAAAGAAATCTAGCCGCAACATATTCAGCATCGTGTTTGTGTTT*t*TTGTCTGTTTTGTA
CCTTACCATATTGCCAGAATCCCCTACACAAAGAGTCAGACCGAAGCTCATTACAGCTGCCA
GTCAAAAGAAATCTTGCGGTATATGAAAGAATTCACTCTG*c*TACTATCTGCTGCAAATGTAT
GCTTGGACCCTATTATTTATTTCTTT*c*TATGCCAGCCGTTTAGGGAAATCTTATGTAAGAAA
TTGCACATTCCATTAAAAGCTCAGAATGACTTAGACATTTCCAGAATCAAAAGAGGAAATAC
AACACTTGAAAGCACAGATACTTTGTAATCTATAT

Figure 2

MINSTSTQPPDESCSQNLLITQQIIPVLYCMVFIAGILLNGVSGWIFFYVPSSKSFIIYLKN
IVIADFVMSLTFPFKILGDSGLGPWQLNVFVCRVSAVLFYVNMYVSIVFFGLISFDRYYKIV
KPLWTSFIQSVSYSKLLSVIVWMLMLLLAVPNIILTNQSVREVTQIKCIELKSELGRKWHKA
SNYIFVAIFWIVFLLLIVFYTAITKKIFKSHLKSSRNSTSVKKKSSRNIFSIVFVFFVCFVP
YHIARIPYTKSQTEAHYSCQSKEILRYMKEFTLLLSAANVCLDPIIYFFLCQPFREILCKKL
HIPLKAQNDLDISRIKRGNTTLESTDTL

Effect of Co-transfection of Galpha-16 with the KIAA0001 Receptor

Agonist Activity of UDP-Glucose and UDP-Galactose on KIAA0001 Receptor

METHODS OF SCREENING FOR AGONISTS AND ANTAGONISTS OF THE INTERACTION BETWEEN THE HUMAN KIAA0001 RECEPTOR AND LIGANDS THEREOF

CROSS-REFERENCE TO RELATED APPLICATION

This application claims benefit to the earlier provisional U.S. Application Ser. No. 60/083,957, filed on May 1, 1998, the contents of which are incorporated herein by reference in their entirety.

FIELD OF THE INVENTION

This invention relates to methods for discovering agonists and antagonists of the interaction between UDP-sugars (e.g.,UDP-glucose, UDP-galactose, UDP-glucuronic acid, and UDP-N-acetyl glucosamine) and their cellular receptor, human KIAA0001 receptor. The invention also relates to the use of the identified agonists, antagonists and/or inhibitors, which are potentially useful in the treatment of human diseases/disorders, including, but not limited to: infections such as bacterial, fungal, protozoan and viral infections, particularly infections caused by HIV-1 or HIV-2; pain; cancers; diabetes, obesity; anorexia; bulimia; asthma; Parkinson's disease; acute heart failure; hypotension; hypertension; urinary retention; osteoporosis; angina pectoris; myocardial infarction; restenosis; atherosclerosis; diseases characterized by excessive smooth muscle cell proliferation; aneurysms; wound healing; diseases characterized by loss of smooth muscle cells or reduced smooth muscle cell proliferation; stroke; ischemia; ulcers; asthma; allergies; benign prostatic hypertrophy; migraine; vomiting; psychotic and neurological disorders, including anxiety, schizophrenia, manic depression, depression, delirium, dementia, and severe mental retardation; degenerative diseases, such as neurodegenerative diseases and dyskinesias, such as Huntington's disease or Gilles dela Tourett's syndrome, among others.

BACKGROUND OF THE INVENTION

It is well established that many medically significant biological processes are mediated by proteins participating in signal transduction pathways that involve G-proteins and/or second messengers, e.g., cAMP (Lefkowitz, *Nature*, 1991, 351:353–354). Herein these proteins are referred to as proteins participating in pathways with G-proteins or PPG proteins. Some examples of these proteins include the G-protein coupled (GPC) receptors, such as those for adrenergic agents and dopamine (Kobilka, B. K., et al., *Proc. Natl Acad. Sci., USA*, 1987, 84:46–50; Kobilka, B. K., et al., *Science*, 1987, 238:650–656; Bunzow, J. R., et al., *Nature*, 1988, 336:783–787), G-proteins themselves, effector proteins, e.g., phospholipase C, adenyl cyclase, and phosphodiesterase, and actuator proteins, e.g., protein kinase A and protein kinase C (Simon, M. I., et al., *Science*, 1991, 252:802–8).

For example, in one form of signal transduction, the effect of hormone binding is activation of the enzyme, adenylate cyclase, inside the cell. Enzyme activation by hormones is dependent on the presence of the nucleotide GTP. GTP also influences hormone binding. A G-protein connects the hormone receptor to adenylate cyclase. G-protein was shown to exchange GTP for bound GDP when activated by a hormone receptor. The GTP-carrying form then binds to activated adenylate cyclase. Hydrolysis of GTh to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The membrane protein gene superfamily of G-protein coupled receptors has been characterized as having seven putative transmembrane domains. The domains are believed to represent transmembrane-helices connected by extracellular or cytoplasmic loops. G-protein coupled receptors include a wide range of biologically active receptors, such as hormone, viral, growth factor and neuroreceptors.

G-protein coupled receptors (otherwise known as 7TM receptors) have been characterized as including these seven conserved hydrophobic stretches of about 20 to 30 amino acids, connecting at least eight divergent hydrophilic loops. The G-protein family of coupled receptors includes dopamine receptors which bind to neuroleptic drugs used for treating psychotic and neurological disorders. Other examples of members of this family include, but are not limited to, calcitonin, adrenergic, endothelin, cAMP, adenosine, muscarinic, acetylcholine, serotonin, histamine, thrombin, kinin, follicle stimulating hormone, opsins, endothelial differentiation gene-1, rhodopsins, odorant, and cytomegalovirus receptors.

Most G-protein coupled receptors have single conserved cysteine residues in each of the first two extracellular loops which form disulfide bonds that are believed to stabilize functional protein structure. The 7 transmembrane regions are designated as TM1, TM2, TM3, TM4, TM5, TM6, and TM7. TM3 has been implicated in signal transduction. Phosphorylation and lipidation (palmitylation or farnesylation) of cysteine residues can influence signal transduction of some G-protein coupled receptors. Most G-protein coupled receptors contain potential phosphorylation sites within the third cytoplasmic loop and/or the carboxy terminus. For several G-protein coupled receptors, such as the β-adrenoreceptor, phosphorylation by protein kinase A and/or specific receptor kinases mediates receptor desensitization.

For some receptors, the ligand binding sites of G-protein coupled receptors are believed to comprise hydrophilic sockets formed by several G-protein coupled receptor transmembrane domains, said socket being surrounded by hydrophobic residues of the G-protein coupled receptors. The hydrophilic side of each G-protein coupled receptor transmembrane helix is postulated to face inward and form polar ligand binding site. TM3 has been implicated in several G-protein coupled receptors as having a ligand binding site, such as the TM3 aspartate residue. TM5 serines, a TM6 asparagine and TM6 or TM7 phenylalanines or tyrosines are also implicated in ligand binding.

G-protein coupled receptors can be intracellularly coupled by heterotrimeric G-proteins to various intracellular enzymes, ion channels and transporters (see Johnson, et al., *Endoc. Rev.*, 1989, 10:317–331) Different G-protein-subunits preferentially stimulate particular effectors to modulate various biological functions in a cell. Phosphorylation of cytoplasmic residues of G-protein coupled receptors have been identified as an important mechanism for the regulation of G-protein coupling of some G-protein coupled receptors. G-protein coupled receptors are found in numerous sites within a mammalian host.

Over the past 15 years, nearly 350 therapeutic agents targeting 7 transmembrane (7TM) receptors have been successfully introduced onto the market.

SUMMARY OF THE INVENTION

In one aspect, the invention relates human KIAA0001 polypeptides and recombinant materials and methods for their production. Another aspect of the invention relates to methods for using such human KIAA0001 polypeptides and polynucleotides. Such uses include the treatment of infections such as bacterial, fungal, protozoan and viral infections, particularly infections caused by HIV-1 or HIV-2; pain; cancers; diabetes, obesity; anorexia; bulimia; asthma; Parkinson's disease; acute heart failure; hypotension; hypertension; urinary retention; osteoporosis; angina pectoris; myocardial infarction; restenosis; atherosclerosis; diseases characterized by excessive smooth muscle cell proliferation; aneurysms; wound healing; diseases characterized by loss of smooth muscle cells or reduced smooth muscle cell proliferation; stroke; ischemia; ulcers; asthma; allergies; benign prostatic hypertrophy; migraine; vomiting; psychotic and neurological disorders, including anxiety, schizophrenia, manic depression, depression, delirium, dementia, and severe mental retardation; degenerative diseases, such as neurodegenerative diseases and dyskinesias, such as Huntington's disease or Gilles dela Tourett's syndrome, among others.

In one aspect, the present invention provides methods of screening for compounds which bind to and activate (agonist) or inhibit activation (antagonist) of human KIAA0001 polypeptides (receptors), and for their ligands, UDP sugars (e.g., UDP-glucose, UDP-galactose, UDP-glucuronic acid, and UDP-N-acetyl glucosamine).

In particular, the preferred method for identifying agonist or antagonist of a human KIAA0001 polypeptide comprises:

(a) contacting a cell expressing on the surface thereof the receptor, said receptor being associated with a second component capable of providing a detectable signal in response to the binding of a compound to said receptor, with a compound to be screened under conditions to permit binding to the polypeptide; and (b) determining whether the compound binds to and activates or inhibits the receptor by measuring the level of a signal generated from the interaction of the compound with the receptor.

In a further preferred embodiment, the method further comprises conducting the identification of an agonist or antagonist in the presence of labeled or unlabeled UDP-sugars (e.g., UDP-glucose, UDP-galactose, UDP-glucuronic acid, and UDP-N-acetyl glucosamine).

In another embodiment of the method for identifying an agonist or antagonist of a human KIAA0001 receptor comprises:

determining the inhibition of binding of a ligand to cells which have the receptor on the surface thereof, or to cell membranes containing the receptor, in the presence of a candidate compound under conditions to permit binding to the receptor, and deternining the amount of ligand bound to the receptor, such that a compound capable of causing reduction of binding of a ligand is an agonist or antagonist. Preferably, the ligand a UDP-sugar (e.g., UDP-glucose, UDP-galactose, UDP-glucuronic acid, or UDP-N-acetyl glucosamine). Yet more preferably, the UDP-sugar (e.g., UDP-glucose, UDP-galactose, UDP-glucuronic acid, or UDP-N-acetyl glucosamine) is labeled.

BRIEF DESCRIPTION OF THE DRAWINGS

FIG. 1 shows the nucleotide sequence of the human KIAA0001 receptor (SEQ ID NO: 1). Bolded nucleotides were deliberately changed by PCR to encode yeast preferred codons.

FIG. 2 shows the deduced amino acid sequence of the human KIAA0001 receptor (SEQ ID NO: 2).

DESCRIPTION OF THE INVENTION

Definitions

Figure 3:
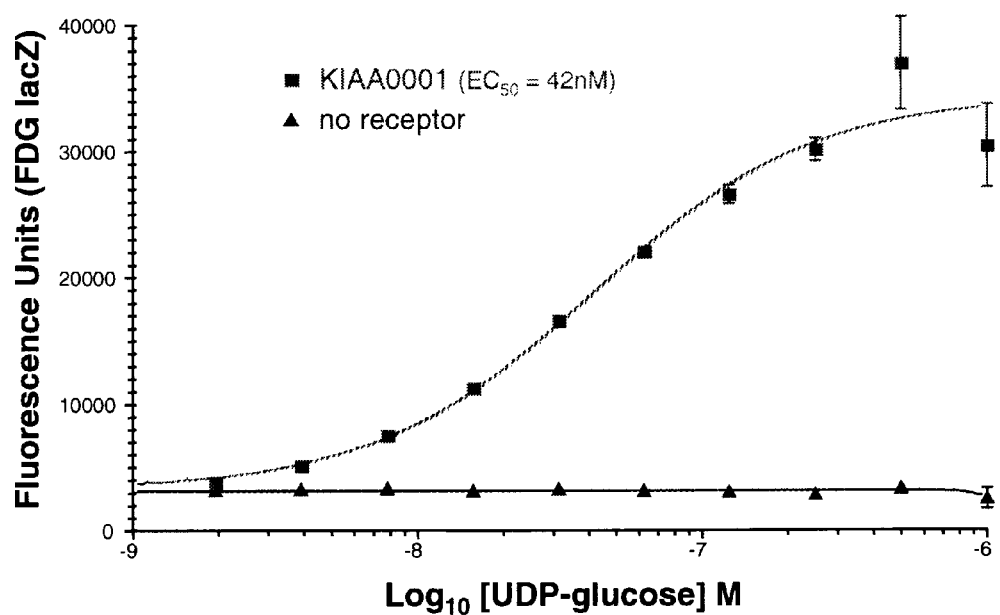
FIG. 3 shows concentration response curves for UDP-glucose against yeast cells containing the pathway-inducible FUS1-LacZ reporter and expressing the human KIAA0001 receptor in combination with GPA1 in a liquid lacZ assay format.

The following definitions are provided to facilitate understanding of certain terms used frequently herein.

"Human KIAA0001" refers generally to polypeptides having the amino acid sequence set forth in SEQ ID NO:2 or an allelic variant thereof.

"UDP sugar" collectively refers to UDP-glucose, UDP-galactose, UDP-glucuronic acid, UDP-N-acetyl glucosamine, and related UDP sugars. The structures of UDP-glucose, UDP-galactose, UDP-glucuronic acid, UDP-N-acetyl glucosamine are shown below:

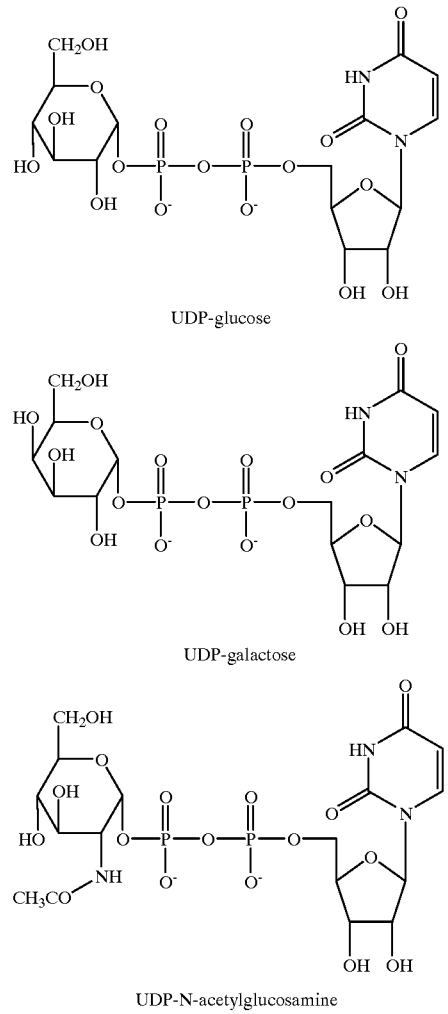

UDP-glucose

UDP-galactose

UDP-N-acetylglucosamine

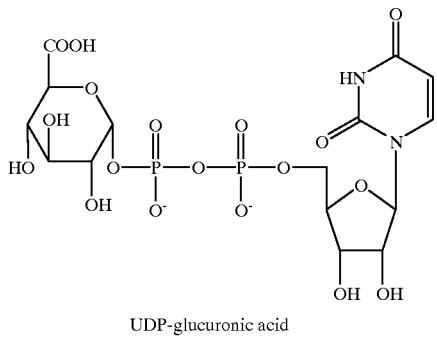

UDP-glucuronic acid

"Receptor Activity" or "Biological Activity of the Receptor" refers to the metabolic or physiologic function of said human KIAA0001, including similar activities or improved activities or these activities with decreased undesirable side-effects. Also included are antigenic and immunogenic activities of said human KIAA0001.

"Human KIAA0001 polypeptides" refers to polypeptides with amino acid sequences sufficiently similar to human KIAA0001, preferably exhibiting at least one biological activity of the receptor.

"Human KIAA0001 gene" refers to a polynucleotide having the nucleotide sequence set forth in SEQ ID NO:1 or allelic variants thereof and/or their complements.

"Human KIAA0001 polynucleotides" and refers to polynucleotides containing a nucleotide sequence which has sufficient identity to a nucleotide sequence contained in SEQ ID NO: 1 to hybridize under conditions useable for amplification or for use as a probe or marker.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Post-translational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter, et al., "Analysis for protein modifications and nonprotein cofactors", *Meth Enzymol* (1990) 182:626–646 and Rattan, et al., "Protein Synthesis: Posttranslational Modifications and Aging", *Ann NY Acad Sci* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.*, 48: 1073 (1988)). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., *Nucleic Acids Research* 12(1): 387 (1984)), BLASTP, BLASTN, and FASTA (Altschul, S. F., et al., *J. Molec. Biol.* 215: 403–410 (1990). The BLAST X program is publicly available from NCBI and other sources (*BLAST Manual*, Altschul, S., et al., NCBI NLM NIH Bethesda, Md. 20894; Altschul, S., et al., *J. Mol. Biol.* 215: 403–410 (1990). The well known Smith Waterman algorithm may also be used to determine identity.

Preferred parameters for polypeptide sequence comparison include the following:

1) Algorithm: Needleman and Wunsch, *J. Mol Biol.* 48: 443–453 (1970)

Comparison matrix: BLOSSUM62 from Hentikoff and Hentikoff, *Proc. Natl. Acad. Sci. USA.* 89:10915–10919 (1992)

Gap Penalty: 12

Gap Length Penalty: 4

A program useful with these parameters is publicly available as the "gap" program from Genetics Computer Group, Madison Wis. The aforementioned parameters are the default parameters for peptide comparisons (along with no penalty for end gaps).

Preferred parameters for polynucleotide comparison include the following:

1) Algorithm: Needleman and Wunsch, *J. Mol Biol.* 48: 443–453 (1970)

Comparison matrix: matches=+10, mismatch=0

Gap Penalty: 50

Gap Length Penalty: 3

Available as: The "gap" program from Genetics Computer Group, Madison Wis. These are the default parameters for nucleic acid comparisons.

By way of example, a polynucleotide sequence of the present invention may be identical to the reference sequence of SEQ ID NO:2, that is it may be 100% identical, or it may include up to a certain integer number of amino acid alterations as compared to the reference sequence such that the percent identity is less than 100% identity. Such alterations are selected from the group consisting of at least one nucleic acid deletion, substitution, including transition and transversion, or insertion, and wherein said alterations may occur at the 5' or 3' terminal positions of the reference polynucleotide sequence or anywhere between those terminal positions, interspersed either individually among the nucleic acids in the reference sequence or in one or more contiguous groups within the reference sequence. The number of nucleic acid alterations for a given percent identity is determined by multiplying the total number of amino acids in SEQ ID NO:2 by the integer defining the percent identity divided by 100 and then subtracting that product from said total number of amino acids in SEQ ID NO:2, or:

$$n_n = x_n - (x_n y),$$

wherein $n_n$ is the number of amino acid alterations, $x_n$ is the total number of amino acids in SEQ ID NO:2, y is, for instance 0.70 for 70%, 0.80 for 80%, 0.85 for 85% etc., is the symbol for the multiplication operator, and wherein any non-integer product of $x_n$ and y is rounded down to the nearest integer prior to subtracting it from $x_n$.

Preferred polypeptide embodiments further include an isolated polypeptide comprising a polypeptide having at least a 50,60, 70, 80, 85, 90, 95, 97 or 100% identity to a polypeptide reference sequence of SEQ ID NO:2, wherein said polypeptide sequence may be identical to the reference sequence of SEQ ID NO:2 or may include up to a certain integer number of amino acid alterations as compared to the reference sequence, wherein said alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids in SEQ ID NO:2 by the integer defining the percent identity divided by 100 and then subtracting that product from said total number of amino acids in SEQ ID NO:2, or:

$$n_a x_a - (x_a y),$$

wherein $n_a$ is the number of amino acid alterations, $x_a$ is the total number of amino acids in SEQ ID NO:2, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and is the symbol for the multiplication operator, and wherein any non-integer product of $x_a$ and y is rounded down to the nearest integer prior to subtracting it from $x_a$.

By way of example, a polypeptide sequence of the present invention may be identical to the reference sequence of SEQ ID NO:2, that is it may be 100% identical, or it may include up to a certain integer number of amino acid alterations as compared to the reference sequence such that the percent identity is less than 100% identity. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the integer defining the percent identity divided by 100 and then subtracting that product from said total number of amino acids in SEQ ID NO:2, or:

$$n_a = x_a - (x_a y),$$

wherein $n_a$ is the number of amino acid alterations, $x_a$ is the total number of amino acids in SEQ ID NO:2, y is, for instance 0.70 for 70%, 0.80 for 80%, 0.85 for 85%, etc., and is the symbol for the multiplication operator, and wherein any non-integer product of $x_a$ and y is rounded down to the nearest integer prior to subtracting it from $x_a$.

Polypeptides of the Invention

The human KIAA0001 polypeptides of the present invention include the polypeptide of SEQ ID NO:2 (in particular the mature polypeptide). The human KIAA0001 polypeptides may be in the form of the "mature" protein or may be a part of a larger protein such as a fusion protein. It is often advantageous to include an additional amino acid sequence which contains secretory or leader sequences, prosequences, sequences which aid in purification such as multiple histidine residues, or an additional sequence for stability during recombinant production.

Biologically active fragments of the human KIAA0001 polypeptides are also included in the invention. A fragment is a polypeptide having an amino acid sequence that entirely is the same as part, but not all, of the amino acid sequence of the aforementioned human KIAA0001 polypeptides. As with human KIAA0001 polypeptides, fragments may be "free-standing," or comprised within a larger polypeptide of which they form a part or region, most preferably as a single continuous region. Representative examples of polypeptide fragments of the invention, include, for example, fragments from about amino acid number 1-20, 21-40, 41-60, 61-80, 81-100, and 101 to the end of human KIAA0001 polypeptides. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of human KIAA0001 polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Biologically active fragments are those that mediate receptor activity, including those with a similar activity or an improved activity, or with a decreased undesirable activity. Also included are those that are antigenic or immunogenic in an animal, especially in a human.

Thus, the polypeptides of the invention include polypeptides having the amino acid sequence set forth in SEQ ID NO:2. Preferably, all of these polypeptides retain the biological activity of the receptor, including antigenic activity. Included in this group are variants of the defined sequence and fragments. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The human KIAA0001 polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to isolated polynucleotides which encode the KIAA0001 polypeptides and polynucleotides closely related thereto.

The nucleotide sequence of SEQ ID NO:1 shows homology with human KIAA0001 receptor (Nomura N., et al., *DNA Res* 1994;1(1):27–35 and Nomura N., et al. *DNA Res* 1994;1(1):47–56). The nucleotide sequence of SEQ ID NO:1 is a cDNA sequence and comprises a polypeptide encoding sequence (nucleotide 1 to 2416) encoding a polypeptide of 338 amino acids, the polypeptide of SEQ ID NO:2. The nucleotide sequence encoding the polypeptide of SEQ ID NO:2 may be identical to the polypeptide encoding sequence contained in SEQ ID NO:1 or it may be a sequence other than the one contained in SEQ ID NO:1, which, as a result of the redundancy (degeneracy) of the genetic code, also encodes the polypeptide of SEQ ID NO:2. The polypeptide of the SEQ ID NO:2 is structurally related to other proteins of the G-coupled Protein Receptors family, having homology and/or structural similarity with human KIAA0001 receptor (Nomura N., et al., *DNA Res* 1994;1 (1):27–35 and Nomura, N., et al., *DNA Res* 1994;1(1):47–56). One polynucleotide of the present invention encoding human KIAA0001 may be obtained using standard cloning and screening, from a cDNA library derived from mRNA in cells of human placenta using the expressed sequence tag (EST) analysis (Adams, M. D., et al. *Science* (1991) 252:1651–1656; Adams, M. D. et al., *Nature*, (1992) 355:632–634; Adams, M. D., et al., *Nature* (1995) 377 Supp:3–174). Polynucleotides of the invention can also be obtained from natural sources such as genomic DNA libraries or can be synthesized using well known and commercially available techniques.

Thus, the nucleotide sequence encoding human KIAA0001 polypeptides may be identical over its entire length to the coding sequence in FIG. 1 (SEQ ID NO:1).

When the polynucleotides of the invention are used for the recombinant production of human KIAA0001 polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre-, or pro- or prepro- protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz, et al., *Proc Natl Acad Sci USA* (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Among particularly preferred embodiments of the invention are polynucleotides encoding human KIAA0001 polypeptides having the amino acid sequence of set out in FIG. 2 (SEQ ID NO:2) and variants thereof.

Further preferred embodiments are polynucleotides encoding human KIAA0001 variants that have the amino acid sequence of the human KIAA0001 of FIG. 2 (SEQ ID NO:2) in which several, 5-10, 1-5, 1-3, 1-2 or 1 amino acid residues are substituted, deleted or added, in any combination.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis, et al., *BASIC METHODS INMOLECULAR BIOLOGY* (1986) and Sambrook, et al., *MOLECULAR CLONING: A LABORATORY MANUAL*, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, *E. coli*, Streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook, et al., *MOLECULAR CLONING, A LABORATORY MANUAL* (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the human KIAA0001 polypeptide is to be expressed for use in screening assays, generally, it is preferred that the polypeptide be produced at the surface of the cell. In this event, the cells may be harvested prior to use in the screening assay. If human KIAA0001 polypeptide is secreted into the medium, the medium can be recovered in order to recover and purify the polypeptide; if produced intracellularly, the cells must first be lysed before the polypeptide is recovered.

Human KIAA0001 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Antibodies

The polypeptides of the invention or their fragments or analogs thereof, or cells expressing them can also be used as immunogens to produce antibodies immunospecific for the human KIAA0001 polypeptides. The term "immunospecific" means that the antibodies have substantially greater affinity for the polypeptides of the invention than their affinity for other related polypeptides in the prior art.

Antibodies generated against the human KIAA0001 polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., *Nature* (1975) 256:495–497), the trioma technique, the human B-cell hybridoma technique (Kozbor, et al., *Immunology Today* (1983) 4:72) and the EBV-hybridoma technique (Cole, et al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against human KIAA0001 polypeptides may also be employed to treat infections such as bacterial, fungal, protozoan and viral infections, particularly infections caused by HIV-1 or HIV-2; pain; cancers; diabetes, obesity; anorexia; bulimia; asthma; Parkinson's disease; acute heart failure; hypotension; hypertension; urinary retention; osteoporosis; angina pectoris; myocardial infarction; restenosis; atherosclerosis; diseases characterized by excessive smooth muscle cell proliferation; aneurysms; wound healing; diseases characterized by loss of smooth muscle cells or reduced smooth muscle cell proliferation; stroke; ischemia;

ulcers; asthma; allergies; benign prostatic hypertrophy; migraine; vomiting; psychotic and neurological disorders, including anxiety, schizophrenia, manic depression, depression, delirium, dementia, and severe mental retardation; degenerative diseases, such as neurodegenerative diseases and dyskinesias, such as Huntington's disease or Gilles dela Tourett's syndrome, among others.

Screening Assays

The human KIAA0001 polypeptide (receptor of the present invention) may be employed in a screening process for compounds which bind the receptor and which activate (agonists) or inhibit activation of (antagonists) the receptor polypeptide of the present invention. Thus, polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See Coligan, et al., Current Protocols in Immunology 1(2):Chapter 5 (1991).

KIAA0001 proteins are ubiquitous in the mammalian host and are responsible for many biological functions, including many pathologies. Accordingly, it is desirous to find compounds and drugs which stimulate KIAA0001 on the one hand and which can inhibit the function of KIAA0001 on the other hand. In general, agonists are employed for therapeutic and prophylactic purposes for such conditions as infections such as bacterial, fungal, protozoan and viral infections, particularly infections caused by HIV-1 or HIV-2; pain; cancers; diabetes, obesity; anorexia; bulimia; asthma; Parkinson's disease; acute heart failure; hypotension; hypertension; urinary retention; osteoporosis; angina pectoris; myocardial infarction; restenosis; atherosclerosis; diseases characterized by excessive smooth muscle cell proliferation; stroke; ischemia; ulcers; asthma; allergies; benign prostatic hypertrophy; migraine; vomiting; psychotic and neurological disorders, including anxiety, schizophrenia, manic depression, depression, delirium, dementia, and severe mental retardation; degenerative diseases, such as neurodegenerative diseases and ischemic stroke; and dyskinesias, such as Huntington's disease or Gilles dela Tourett's syndrome, among others. Antagonists may be employed for a variety of therapeutic and prophylactic purposes for such conditions as bacterial, fungal, protozoan and viral infections, particularly infections caused by HIV-1 or HIV-2; pain; cancers; diabetes, obesity; anorexia; bulimia; asthma; Parkinson's disease; acute heart failure; hypotension; hypertension; urinary retention; osteoporosis; angina pectoris; myocardial infarction; restenosis; aneurysms; wound healing; diseases characterized by loss of smooth muscle cells or reduced smooth muscle cell proliferation; stroke; ischemia; ulcers; asthma; allergies; benign prostatic hypertrophy; migraine; vomiting; psychotic and neurological disorders, including anxiety, schizophrenia, manic depression, depression, delirium, dementia, and severe mental retardation; degenerative diseases, such as neurodegenerative diseases and dyskinesias, such as Huntington's disease or Gilles dela Tourett's syndrome, among others.

In general, such screening procedures involve providing appropriate cells which express a receptor polypeptide of the present invention on the surface thereof. Such cells include cells from mammals, yeast, Drosophila or E. coli. In particular, a polynucleotide encoding the receptor of the present invention is employed to transfect cells to thereby express a human KIAA0001 polypeptide. The expressed receptor is then contacted with a test compound to observe binding, stimulation or inhibition of a functional response.

One such screening procedure involves the use of melanophores which are transfected to express the human KIAA0001 polypeptide. Such a screening technique is described in PCT WO 92/01810, published Feb. 6, 1992. Such an assay may be employed to screen for a compound which inhibits activation of a receptor of the present invention by contacting the melanophore cells which encode the receptor with both a receptor ligand, such as UDP-glucose, and a compound to be screened. Inhibition of the signal generated by the ligand indicates that a compound is a potential antagonist for the receptor, i.e., inhibits activation of the receptor.

The technique may also be employed for screening of compounds which activate a receptor of the present invention by contacting such cells with compounds to be screened and determining whether such compound generates a signal, i.e., activates the receptor.

Other screening techniques include the use of cells which express the human KIAA0001 polypeptide receptor (for example, transfected CHO cells) in a system which measures extracellular pH changes caused by receptor activation. In this technique, compounds may be contacted with cells expressing a receptor polypeptide of the present invention. A second messenger response, e.g., signal transduction or pH changes, is then measured to determine whether the potential compound activates or inhibits the receptor.

Another screening technique involves expressing a human KIAA0001 polypeptide in which the receptor is linked to phospholipase C or D. Representative examples of such cells include, but are not limited to, endothelial cells, smooth muscle cells, and embryonic kidney cells. The screening may be accomplished as hereinabove described by detecting activation of the receptor or inhibition of activation of the receptor from the phospholipase second signal.

Another method involves screening for compounds which are antagonists, and thus inhibit activation of a receptor polypeptide of the present invention by determining inhibition of binding of labeled ligand, such as UDP-sugars (e.g., UDP-glucose, UDP-galactose, UDP-glucuronic acid, and UDP-N-acetyl glucosamine), to cells which have the receptor on the surface thereof, or cell membranes containing the receptor. Such a method involves transfecting a eukaryotic cell with a DNA encoding a human KIAA0001 polypeptide such that the cell expresses the receptor on its surface. The cell is then contacted with a potential antagonist in the presence of a labeled form of a ligand, such a UDP-sugar (e.g., UDP-glucose, UDP-galactose, UDP-glucuronic acid, and UDP-N-acetyl glucosamine). The ligand can be labeled, e.g., by radioactivity. The amount of labeled ligand bound to the receptors is measured, e.g., by measuring radioactivity associated with transfected cells or membrane from these cells. If the compound binds to the receptor, the binding of labeled ligand to the receptor is inhibited as determined by a reduction of labeled ligand which binds to the receptors. This method is called binding assay.

Another such screening procedure involves the use of mammalian cells which are transfected to express a receptor of the present invention. The cells are loaded with an indicator dye that produces a fluorescent signal when bound to calcium, and the cells are contacted with a test substance and a receptor agonist, such a UDP-sugar (e.g., UDP-glucose, UDP-galactose, UDP-glucuronic acid, and UDP-N-acetyl glucosamine). Any change in fluorescent signal is measured over a defined period of time using, for example, a fluorescence spectrophotometer or a fluorescence imaging plate reader. A change in the fluorescence signal pattern generated by the ligand indicates that a compound is a potential antagonist (or agonist) for the receptor.

Another such screening procedure involves use of mammalian cells which are transfected to express a receptor of the present invention, and which are also transfected with a reporter gene construct that is coupled to activation of the receptor (for example, luciferase or beta-galactosidase behind an appropriate promoter). The cells are contacted with a test substance and a receptor agonist, such a UDP-sugar (e.g., UDP-glucose, UDP-galactose, UDP-glucuronic acid, and UDP-N-acetyl glucosamine), and the signal produced by the reporter gene is measured after a defined period of time. The signal can be measured using a luminometer, spectrophotometer, fluorimeter, or other such instrument appropriate for the specific reporter construct used. Inhibition of the signal generated by the ligand indicates that a compound is a potential antagonist for the receptor.

Another such screening technique for antagonists or agonists involves introducing RNA encoding the human KIAA0001 polypeptide into Xenopus oocytes to transiently or stably express the receptor. The receptor oocytes are then contacted with a receptor ligand, such a UDP-sugar (e.g., UDP-glucose, UDP-galactose, UDP-glucuronic acid, and UDP-N-acetyl glucosamine), and a compound to be screened. Inhibition or activation of the receptor is then determined by detection of a signal, such as, cAMP, calcium, proton, or other ions.

Another method involves screening for human KIAA0001 polypeptide inhibitors by determining inhibition or stimulation of human KIAA0001 polypeptide-mediated cAMP and/or adenylate cyclase accumulation or dimunition. Such a method involves transiently or stably transfecting a eukaryotic cell with a human KIAA0001 polypeptide to express the receptor on the cell surface. The cell is then exposed to potential antagonists in the presence of KIAA0001 polypeptide ligand, such a UDP-sugar (e.g., UDP-glucose, UDP-galactose, UDP-glucuronic acid, and UDP-N-acetyl glucosamine). The amount of cAMP accumulation is then measured, for example, by radio-immuno or protein binding assays (e.g., using Flashplates or a scintillation proximity assay). Changes in cAMP levels can also be determined by directly measuring the activity of the enzyme, adenyl cyclase, in broken cell preparations. If the potential antagonist binds the receptor, and thus inhibits human KIAA0001 polypeptide binding, the levels of human KIAA0001 polypeptide-mediated cAMP, or adenylate cyclase activity, will be reduced or increased.

Another screening method for agonists and antagonists relies on the endogenous pheromone response pathway in the yeast, *Saccharomyces cerevisiae*. Heterothallic strains of yeast can exist in two mitotically stable haploid mating types, MATa and MATα. Each cell type secretes a small peptide hormone that binds to a G-protein coupled receptor on opposite mating-type cells which triggers a MAP kinase cascade leading to GI arrest as a prelude to cell fusion. Genetic alteration of certain genes in the pheromone response pathway can alter the normal response to pheromone, and heterologous expression and coupling of human G-protein coupled receptors and humanized G-protein subunits in yeast cells devoid of endogenous pheromone receptors can be linked to downstream signaling pathways and reporter genes (e.g., U.S. Pat. Nos. 5,063,154; 5,482,835; 5,691,188). Such genetic alterations include, but are not limited to, (i) deletion of the STE2 or STE3 gene encoding the endogenous G-protein coupled pheromone receptors; (ii) deletion of the FAR1 gene encoding a protein that normally associates with cyclin-dependent kinases leading to cell cycle arrest; and (iii) construction of reporter genes fused to the FUS1 gene promoter (where FUS1 encodes a membrane-anchored glycoprotein required for cell fusion). Downstream reporter genes can permit either a positive growth selection (e.g., histidine prototrophy using the FUS1-HIS3 reporter), or a colorimetric, fluorimetric or spectrophotometric readout, depending on the specific reporter construct used (e.g., b-galactosidase induction using a FUS1-LacZ reporter).

The yeast cells can be further engineered to express and secrete small peptides from random peptide libraries, some of which can permit autocrine activation of heterologously expressed human (or mammalian) G-protein coupled receptors (Broach, J. R. and Thorner, J. *Nature* 384: 14–16, 1996; Manfredi, et al., *Mol. Cell. Biol.* 16: 4700–4709, 1996). This provides a rapid direct growth selection (e.g,, using the FUS1-HIS3 reporter) for surrogate peptide agonists that activate characterized or orphan receptors. Alternatively, yeast cells that functionally express human (or mammalian) G-protein coupled receptors linked to a reporter gene readout (e.g., FUS1-LacZ) can be used as a platform for high-throughput screening of known ligands, fractions of biological extracts and libraries of chemical compounds for either natural or surrogate ligands. Functional agonists of sufficient potency (whether natural or surrogate) can be used as screening tools in yeast cell-based assays for identifying G-protein coupled receptor antagonists. For this purpose, the yeast system offers advantages over mammalian expression systems due to its ease of utility and null receptor background (lack of endogenous G-protein coupled receptors) which often interferes with the ability to identify agonists or antagonists.

The present invention also provides a method for determining whether a ligand not known to be capable of binding to a human KIAA0001 polypeptide can bind to such receptor which comprises contacting a yeast or mammalian cell which expresses a human KIAA0001 polypeptide with the ligand, such a UDP-sugar (e.g., UDP-glucose, UDP-galactose, UDP-glucuronic acid, and UDP-N-acetyl glucosamine), under conditions permitting binding of candidate ligands to a human KIAA0001 polypeptide, and detecting the presence of a candidate ligand which binds to the receptor, thereby determining whether the ligand binds to the human KIAA0001 polypeptide. The systems hereinabove described for determining agonists and/or antagonists may also be employed for determining ligands which bind to the receptor.

The present invention also contemplates agonists and antagonists obtainable from the above described screening methods.

Examples of potential human KIAA0001 polypeptide antagonists include antibodies or, in some cases, oligonucleotides, which bind to the receptor but do not elicit a second messenger response such that the activity of the receptor is prevented. Potential antagonists also include compounds which are closely related to a ligand of the human KIAA0001 polypeptide, i.e. a fragment of the ligand, which has lost biological function and when binding to the human KIAA0001 polypeptide, elicits no response.

Thus, in another aspect, the present invention relates to a screening kit for identifying agonists, antagonists, and ligands for KIAA0001 polypeptides, which comprises:

(a) a KIAA0001 polypeptide, preferably that of SEQ ID NO:2; and further preferably comprises a labeled or unlabeled UDP-sugar (e.g., UDP-glucose, UDP-galactose, UDP-glucuronic acid, and UDP-N-acetyl glucosamine);

(b) a recombinant cell expressing a KIAA0001 polypeptide, preferably that of SEQ ID NO:2; and further preferably comprises labeled or unlabeled UDP-sugar (e.g., UDP-glucose, UDP-galactose, UDP-glucuronic acid, and UDP-N-acetyl glucosamine); or (c) a cell membrane expressing KIAA0001 polypeptide; preferably that of SEQ ID NO: 2; and further preferably comprises a labeled or unlabeled UDP-sugar (e.g., UDP-glucose, UDP-galactose, UDP-glucuronic acid, and UDP-N-acetyl glucosamine).

It will be appreciated that in any such kit, (a), (b), or (c) may comprise a substantial component.

Potential antagonists also include soluble forms of KIAA0001 polypeptide receptor, e.g., fragments of the receptor, which bind to the ligand and prevent the ligand from interacting with membrane bound KIAA0001 polypeptide receptors.

A potential antagonist also includes an antisense construct prepared through the use of antisense technology. Antisense technology can be used to control gene expression through triple-helix formation or antisense DNA or RNA, both methods of which are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee, et al. *Nucl. Acids Res.*, 6: 3073 (1979); Cooney, et al, *Science*, 241: 456 (1988); and Dervan, et al., *Science*, 251: 1360 (1991)), thereby preventing transcription and production of a KIAA0001 receptor polypeptide. The antisense RNA oligonucleotide hybridizes to the mRNA in vivo and blocks translation of the mRNA molecule to KIAA0001 polypeptide (antisense—Okano, J., *Neurochem.*, 56: 560 (1991); OLIGODEOXYNUCLEOTIDES AS ANTISENSE INHIBITORS OF GENE EXPRESSION, CRC Press, Boca Raton, Fla. (1988)). The oligonucleotides described above can also be delivered to cells such that the antisense RNA or DNA may be expressed in vivo to inhibit production of a human KIAA0001 polypeptide.

Prophylactic and Therapeutic Methods

This invention provides methods of treating an abnormal conditions related to both an excess of and insufficient amounts of human KIAA0001 receptor activity.

If the activity of human KIAA0001 receptor is in excess, several approaches are available. One approach comprises administering to a subject an inhibitor compound (antagonist) as hereinabove described along with a pharmaceutically acceptable carrier in an amount effective to inhibit activation by blocking binding of ligands to the human KIAA0001 receptor, or by inhibiting a second signal, and thereby alleviating the abnormal condition.

In another approach, soluble forms of human KIAA0001 polypeptides still capable of binding the ligand in competition with endogenous human KIAA0001 may be administered. Typical embodiments of such competitors comprise fragments of the human KIAA0001 polypeptide.

In still another approach, expression of the gene encoding endogenous human KIAA0001 can be inhibited using expression blocking techniques. Known such techniques involve the use of antisense sequences, either internally generated or separately administered. See, for example, O'Connor, *J Neurochem* (1991) 56:560 in *Oligodeoxynucleotides as Antisense Inhibitors of Gene Expression*, CRC Press, Boca Raton, Fla. (1988). Alternatively, oligonucleotides which form triple helices with the gene can be supplied. See, for example, Lee, et al., *Nucleic Acids Res* (1979) 6:3073; Cooney et al., *Science* (1988) 241:456; Dervan, et al., *Science* (1991) 251:1360. These oligomers can be administered per se or the relevant oligomers can be expressed in vivo.

For treating abnormal conditions related to an under-expression of human KIAA0001 receptor and its activity, several approaches are also available. One approach comprises administering to a subject a therapeutically effective amount of a compound which activates human KIAA0001 receptor, i.e., an agonist as described above, in combination with a pharmaceutically acceptable carrier, to thereby alleviate the abnormal condition. Alternatively, gene therapy may be employed to effect the endogenous production of human KIAA0001 receptor by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches*, (and references cited therein) in Human Molecular Genetics, T Strachan and A P Read, BIOS Scientific Publishers Ltd. (1996).

Formulation and Administration

Peptides, such as the soluble form of human KIAA0001 polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 $\mu$g/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

EXAMPLES

Example 1

Yeast Cell Expression

The receptor of the present invention was constitutively expressed in *Saccharomyces cerevisiae* using the PGK1 promoter carried on a standard 2-micron-based *S. cerevisiae-E.coli* shuttle plasmid containing the gene for ampillicin resistance, the ColE1 origin of replication and the *S. cerevisiae* LEU2 gene. The human KIAA0001 cDNA was modified by trimming away the 5' and 3' UTRs and subcloned into the yeast expression vector. Following introduction into yeast cells using standard yeast genetic techniques, human KIAA0001 polypeptide expression was detected by western blotting using a C-terminally tagged human KIAA0001 construct and antibodies to the epitope tag. Functional expression of human KIAA0001 polypeptide (untagged) was determined as described in Example 8.

Example 2

Ligand Bank for Binding and Functional Assays

A bank of over 200 putative receptor ligands has been assembled for screening. The bank comprises: transmitters, hormones and chemokines known to act via a human seven transmembrane (7TM) receptor; naturally occurring compounds which may be putative agonists for a human 7TM receptor; non-mammalian, biologically active peptides for which a mammalian counterpart has not yet been identified; and compounds not found in nature, but which activate 7TM receptors with unknown natural ligands. This bank is used to initially screen the receptor for known ligands, using both functional (i.e., calcium, cAMP, microphysiometer, oocyte electrophysiology, etc., see below) as well as binding assays.

Example 3

Ligand Binding Assays

Ligand binding assays provide a direct method for ascertaining receptor pharmacology and are adaptable to a high throughput format. The purified ligand for a receptor is radiolabeled to high specific activity (50–2000 Ci/mmol) for binding studies. A determination is then made that the process of radiolabeling does not diminish the activity of the ligand towards its receptor. Assay conditions for buffers, ions, pH and other modulators such as nucleotides are optimized to establish a workable signal to noise ratio for both membrane and whole cell receptor sources. For these assays, specific receptor binding is defined as total associated radioactivity minus the radioactivity measured in the presence of an excess of unlabeled competing ligand. Where possible, more than one competing ligand is used to define residual nonspecific binding.

Example 4

Functional Assay in *Xenopus* Oocytes

Capped RNA transcripts from linearized plasmid templates encoding the receptor cDNAs of the invention are synthesized in vitro with RNA polymerases in accordance with standard procedures. In vitro transcripts are suspended in water at a final concentration of 0.2 mg/ml. Ovarian lobes are removed from adult female toads, Stage V defolliculated oocytes are obtained, and RNA transcripts (10 ng/oocyte) are injected in a 50 nl bolus using a microinjection apparatus. Two electrode voltage clamps are used to measure the currents from individual Xenopus oocytes in response to agonist exposure. Recordings are made in Ca2+ free Barth's medium at room temperature. The Xenopus system can be used to screen known ligands and tissue/cell extracts for activating ligands.

Example 5

Microphysiometric Assays

Activation of a wide variety of secondary messenger systems results in extrusion of small amounts of acid from a cell. The acid formed is largely as a result of the increased metabolic activity required to fuel the intracellular signaling process. The pH changes in the media surrounding the cell are very small but are detectable by the CYTOSENSOR microphysiometer (Molecular Devices Ltd., Menlo Park, Calif.). The CYTOSENSOR is thus capable of detecting the activation of a receptor which is coupled to an energy utilizing intracellular signaling pathway such as the G-protein coupled receptor of the present invention.

Example 6

Extract/Cell Supernatant Screening

A large number of mammalian receptors exist for which there remains, as yet, no cognate activating ligand (agonist). Thus, active ligands for these receptors may not be included within the ligands banks as identified to date. Accordingly, the 7TM receptor of the invention is also functionally screened (using calcium, cAMP, microphysiometer, oocyte electrophysiology, etc., functional screens) against tissue extracts to identify natural ligands. Extracts that produce positive functional responses can be sequentially subfractionated until an activating ligand is isolated or identified.

Example 7

Calcium and cAMP Functional Assays

7TM receptors which are expressed in HEK 293 cells have been shown to be coupled functionally to activation of PLC and calcium mobilization and/or cAMP stimulation or inhibition. Basal calcium levels in the HEK 293 cells in receptor-transfected or vector control cells were observed to be in the normal, 100 nM to 200 nM, range. HEK 293 cells expressing recombinant receptors are loaded with fura 2 and in a single day>150 selected ligands or tissue/cell extracts are evaluated for agonist induced calcium mobilization. Similarly, HEK 293 cells expressing recombinant receptors are evaluated for the stimulation or inhibition of cAMP production using standard cAMP quantitation assays. Agonists presenting a calcium transient or cAMP fluctuation are tested in vector control cells to determine if the response is unique to the transfected cells expressing receptor.

Figure 4A:
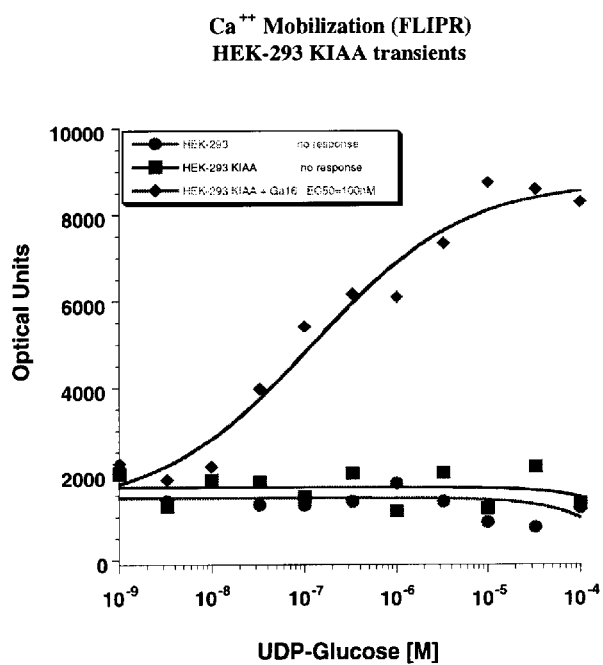
FIGS. 4A and 4B show concentration response curves for UDP-glucose and UDP-galactose against HEK293 cells transiently transfected with the human KIAA0001 receptor.
Figure 4B:
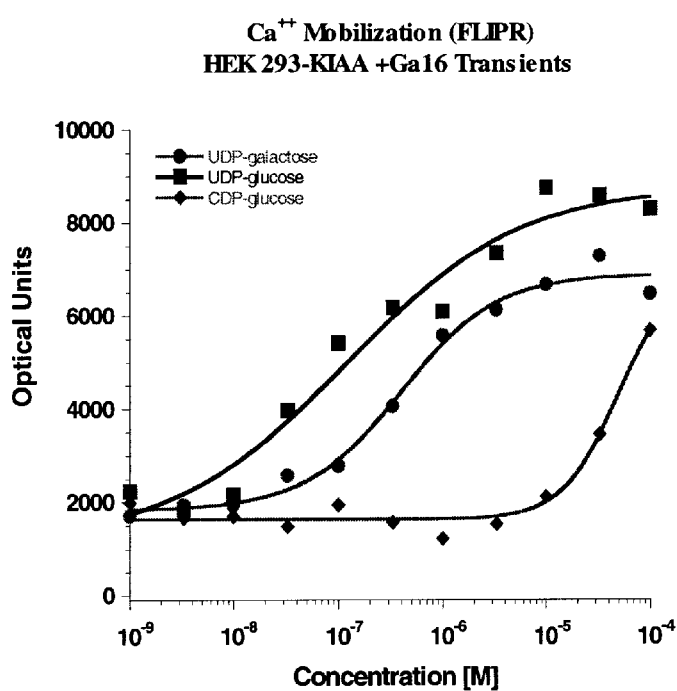

The KIAA0001 receptor was transiently transfected into HEK 293 cells or co-transfected with G·16. FIG. 4A shows that the calcium functional response for UDP-glucose required co-transfection with G·16. The HEK 293 parental cell line and the HEK 293 cells transfected with only the receptor did not respond to UDP-glucose. Two ligands, UDP-glucose and UDP-galactose, were identified as potent agonists for HEK 293 cells co-transfected with KIAA0001 receptor and G·16, per the result shown in FIG. 4B. The $EC_{50}$ (concentration that gives 50% of the maximal response) for these ligands was approximately 300 nM. FIG. 4B shows that the cells did respond with low potency to CDP-glucose with an approximate $EC_{50}$ of 50,000 nM.

Example 8

UDP-suzar (e.g., UDP-glucose, UDP-galactose, UDP-glucuronic acid, and UDP-N-acetyl glucosamine)-induced Reporter Gene Expression in Yeast Human KIAA0001 receptor was expressed in yeast strains containing endogenous yeast G-proteins and/or co-expressed yeast/human chimeric G proteins, and/or human G-proteins. The yeast strain(s) used contain mutations in genes in the pheromone response pathway, e.g., (i) deletion of the STE2 or STE3 gene encoding the endogenous G-protein coupled pheromone receptors; (ii) deletion of the FAR1 gene encoding a protein that normally associates with cyclin-dependent kinases leading to cell cycle arrest; and (iii) construction of reporter genes fused to the FUS1 gene promoter (where FUS1 encodes a membrane-anchored glycoprotein required for cell fusion). The downstream reporter (FUS1-LacZ) permits a colorimetric or fluorimetric readout in response to ligand. FUS1-LacZ yeast expressing human KIAA0001 receptor demonstrated a receptor-dependent response to UDP-sugars (e.g., UDP-glucose, UDP-galactose, UDP-glucuronic acid, and UDP-N-acetyl glucosamine) as determined by the expression of -galactosidase. The response to UDP-glucose, which is shown in FIG. 3, indicates functional coupling of the human KIAA0001 receptor to yeast or yeast/human chimeric G-proteins.

The specificity of this response was determined by spotting 10 nmoles (1 microliter of 10 mM solution) of each nucleotide di-phosphate sugar onto an agar plate infused with a yeast strain carrying the human KIAA0001 receptor and the FUS1-LacZ reporter, as described above. UDP-glucose, UDP-galactose, UDP-glucuronic acid and UDP-acetylglucosamine produced a positive response, while ADP-ribose, GDP-glucose, ADP-glucose, ADP-mannose, GDP-fucose, CDP-glucose, GDP-mannose, and TDP-glucose failed to produce a response.

Example 9

Effects of UDP-glucose on the Proliferation of Cultured Human Aorta Smooth Muscle Cells Studies were conducted to evaluate the effects of UDP-glucose on the proliferation of cultured human aorta smooth muscle cells (HASMCs). Results indicated a significant reduction of cell proliferation from 1–10 uM in a dose-dependent manner, as measured by tritiated thymidine uptake. The tritiated thymidine uptake studies were performed as described by Sung, et al., *Journal of Pharmacology and Experimental Therapeutics* 271: 429–437 (1994). The maximum dose evaluated, 10 uM, caused a 27% reduction in cell proliferation. The HCASMCs were purchased from Clonetics (San Diego, Calif.) and cultured according to the supplier's instructions.

The results from this experiment reveail that diseases in which an agonist of UDP-glucose would be advantageous would be restenosis, atherosclerosis, and other diseases characterized by excessive smooth muscle cell proliferation. An antagonist of UDP-glucose would be advantageous for diseases, including aneurysms, wound healing, and other diseases characterized by loss of smooth muscle cells or reduced smooth muscle cell proliferation.

All publications including, but not limited to, patents and patent applications, cited in this specification, are herein incorporated by reference as if each individual publication were specifically and individually indicated to be incorporated by reference herein as though fully set forth. The above description fully discloses the invention, including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore, the examples provided herein are to be construed as merely illustrative and are not a limitation of the scope of the present invention in any way. The embodiments of the invention in which an exclusive property or privilege is claimed are defined as follows.

What is claimed is:

1. A method for identifying an agonist or antagonist of the KIAA0001 polypeptide set forth in SEQ ID NO:2, said method comprising the steps of:
   (a) contacting a cell expressing on the surface thereof the polypeptide, said polypeptide being associated with a second component capable of providing a detectable signal in response to the binding of a compound to said polypeptide, with a compound to be screened under conditions to permit binding to the polypeptide in the presence of a labeled or unlabeled UDP sugar selected from the group consisting of: UDP-glucose, UDP-galactose, UDP-glucoronic acid, and UDP-N-acetyl glucosamine; and
   (b) determining whether the compound binds to and activates or inhibits the polypeptide by measuring the level of a signal generated from the interaction of the compound with the polypeptide, thereby identifying an agonist or antagonist of the polypeptide set forth in SEQ ID NO:2.

2. The method of claim 1, wherein the cell is a mammalian cell.

3. The method of claim 2, wherein the cell is a mammalian HEK293 cell.

4. A method for identifying an agonist or antagonist of the KIAA0001 polypeptide set forth in SEQ ID NO:2, said method comprising the steps of:
   (a) determining the inhibition of binding of a ligand to cells having the polypeptide on the surface thereof, or to cell membranes containing the polypeptide, in the presence of a candidate compound and a labeled or unlabeled UDP sugar selected from the group consisting of: UDP-glucose, UDP-galactose, UDP-glucoronic acid, and UDP-N-acetyl glucosamine, under conditions to permit binding to the polypeptide; and
   (b) determining the amount of ligand bound to the polypeptide, such that a compound that causes the reduction of binding of a ligand is an agonist or antagonist of the KIAA0001 polypeptide set forth in SEQ ID NO:2.

5. The method of claim 4, wherein the cell is a mammalian cell.

6. The method of claim 5, wherein the cell is a mammalian HEK293 cell.

* * * * *

SEQUENCE LISTING

```
<160> NUMBER OF SEQ ID NOS: 2

<210> SEQ ID NO 1
<211> LENGTH: 1027
<212> TYPE: DNA
<213> ORGANISM: Homo sapiens

<400> SEQUENCE: 1
atcatgatta attctacttc cacacagcct ccagatgaat cctgctctca gaacctcctg      60
atcactcagc agatcattcc tgtgctgtac tgtatggtct tcattgcagg aatcctactc     120
aatggagtgt caggatggat attcttttac gtgcccagct ctaagagttt catcatctat     180
ctcaagaaca ttgttattgc tgactttgtg atgagcctga cttttccttt caagatcctt     240
ggtgactcag gccttggtcc ctggcagctg aacgtgtttg tgtgcagggt ctctgccgtg     300
ctcttctacg tcaacatgta cgtcagcatt gtgttctttg ggctcatcag ctttgacaga     360
tattataaaa ttgtaaagcc tctttggact tctttcatcc agtcagtgag ttacagcaaa     420
cttctgtcag tgatagtatg gatgctcatg ctcctccttg ctgttccaaa tattattctc     480
```

```
accaaccaga gtgttaggga ggttacacaa ataaaatgta tagaactgaa aagtgaactg    540
ggacggaagt ggcacaaagc atcaaactac atcttcgtgg ccatcttctg gatagtgttt    600
cttttgttaa tcgttttcta tactgctatc acaaagaaaa tctttaagtc ccaccttaag    660
tcaagtcgga attccacttc ggtcaaaaag aaatctagcc gcaacatatt cagcatcgtg    720
tttgtgtttt ttgtctgttt tgtaccttac catattgcca gaatccccta cacaaagagt    780
cagaccgaag ctcattacag ctgccagtca aagaaatct tgcggtatat gaaagaattc     840
actctgctac tatctgctgc aaatgtatgc ttggacccta ttatttattt ctttctatgc    900
cagccgttta gggaaatctt atgtaagaaa ttgcacattc cattaaaagc tcagaatgac    960
ttagacattt ccagaatcaa agaggaaat acaacacttg aaagcacaga tactttgtaa    1020
tctatat                                                              1027
```

<210> SEQ ID NO 2
<211> LENGTH: 338
<212> TYPE: PRT
<213> ORGANISM: Homo sapiens

<400> SEQUENCE: 2

```
Met Ile Asn Ser Thr Ser Thr Gln Pro Pro Asp Glu Ser Cys Ser Gln
  1               5                  10                  15

Asn Leu Leu Ile Thr Gln Gln Ile Ile Pro Val Leu Tyr Cys Met Val
                 20                  25                  30

Phe Ile Ala Gly Ile Leu Leu Asn Gly Val Ser Gly Trp Ile Phe Phe
             35                  40                  45

Tyr Val Pro Ser Ser Lys Ser Phe Ile Ile Tyr Leu Lys Asn Ile Val
 50                  55                  60

Ile Ala Asp Phe Val Met Ser Leu Thr Phe Pro Phe Lys Ile Leu Gly
 65                  70                  75                  80

Asp Ser Gly Leu Gly Pro Trp Gln Leu Asn Val Phe Val Cys Arg Val
                 85                  90                  95

Ser Ala Val Leu Phe Tyr Val Asn Met Tyr Val Ser Ile Val Phe Phe
            100                 105                 110

Gly Leu Ile Ser Phe Asp Arg Tyr Tyr Lys Ile Val Lys Pro Leu Trp
            115                 120                 125

Thr Ser Phe Ile Gln Ser Val Ser Tyr Ser Lys Leu Leu Ser Val Ile
            130                 135                 140

Val Trp Met Leu Met Leu Leu Leu Ala Val Pro Asn Ile Ile Leu Thr
145                 150                 155                 160

Asn Gln Ser Val Arg Glu Val Thr Gln Ile Lys Cys Ile Glu Leu Lys
                165                 170                 175

Ser Glu Leu Gly Arg Lys Trp His Lys Ala Ser Asn Tyr Ile Phe Val
            180                 185                 190

Ala Ile Phe Trp Ile Val Phe Leu Leu Leu Ile Val Phe Tyr Thr Ala
            195                 200                 205

Ile Thr Lys Lys Ile Phe Lys Ser His Leu Lys Ser Ser Arg Asn Ser
            210                 215                 220

Thr Ser Val Lys Lys Ser Arg Asn Ile Phe Ser Ile Val Phe
225                 230                 235                 240

Val Phe Phe Val Cys Phe Val Pro Tyr His Ile Ala Arg Ile Pro Tyr
                245                 250                 255

Thr Lys Ser Gln Thr Glu Ala His Tyr Ser Cys Gln Ser Lys Glu Ile
            260                 265                 270
```

-continued

```
Leu Arg Tyr Met Lys Glu Phe Thr Leu Leu Leu Ser Ala Ala Asn Val
        275                 280                 285

Cys Leu Asp Pro Ile Ile Tyr Phe Phe Leu Cys Gln Pro Phe Arg Glu
    290                 295                 300

Ile Leu Cys Lys Lys Leu His Ile Pro Leu Lys Ala Gln Asn Asp Leu
305                 310                 315                 320

Asp Ile Ser Arg Ile Lys Arg Gly Asn Thr Thr Leu Glu Ser Thr Asp
                325                 330                 335

Thr Leu
```